United States Patent [19]

Yamamoto et al.

[11] Patent Number: 5,356,620
[45] Date of Patent: Oct. 18, 1994

[54] PHARMACEUTICAL COMPOSITIONS CONTAINING N-(3,4-DIMETHOXYCINNAMOYL) ANTHRANILIC ACID

[75] Inventors: Tokihiko Yamamoto, Nagoya; Taihei Shibazaki, Toyoake; Yukiyoshi Ajisawa, Okaya; Ryoji Yamamoto; Yukihiko Kinoshita, both of Matsumoto, all of Japan

[73] Assignees: Kissei Pharmaceutical Co. Ltd.; Nitten Ophthalmic Research Institute Company, both of Japan

[21] Appl. No.: 680,786

[22] Filed: Apr. 3, 1991

Related U.S. Application Data

[63] Continuation of Ser. No. 432,911, Nov. 7, 1989, abandoned.

[30] Foreign Application Priority Data

Apr. 4, 1989 [JP] Japan .................... 1-085521

[51] Int. Cl.$^5$ .................. A61K 31/16; A61K 31/185
[52] U.S. Cl. ........................... 424/78.04; 424/78.05; 514/563; 514/567
[58] Field of Search ............ 424/80, 78, 78.35, 78.04, 424/78.05; 514/563, 567, 714

[56] References Cited

U.S. PATENT DOCUMENTS

| | | | |
|---|---|---|---|
| 3,856,919 | 12/1974 | Rankin | 424/80 |
| 4,029,817 | 6/1977 | Blanco et al. | 424/80 |
| 4,070,484 | 1/1978 | Harita et al. | 514/563 |
| 4,666,929 | 5/1987 | Sato et al. | 524/471 |

FOREIGN PATENT DOCUMENTS 6144811  3/1986  Japan .
WO88/04922  7/1988  PCT Int'l Appl. .

*Primary Examiner*—G. S. Kishore
*Assistant Examiner*—Peter F. Kulkosky
*Attorney, Agent, or Firm*—Depaoli & O'Brien

[57] ABSTRACT

In preferred embodiments this invention provides a pharmaceutical composition and a method for the treatment of allergic conjunctivitis or allergic rhinitis. The composition is an aqueous solution containing N-(3,4-dimethoxycinnamoyl)anthranilic acid or a pharmaceutically acceptable salt thereof as an active ingredient. The composition additionally contains as essential components polyvinylpyrrolidone, a basic compound and a surface active agent in prescribed quantities, and the composition has a pH of about 6.5-8.5.

3 Claims, No Drawings

PHARMACEUTICAL COMPOSITIONS CONTAINING N-(3,4-DIMETHOXYCINNAMOYL) ANTHRANILIC ACID

This application is a continuation of application Ser. No. 07/432,911, filed Nov. 7, 1989, now abandoned.

FIELD OF THE INVENTION

This invention relates to pharmaceutical compositions containing N-(3,4-dimethoxycinnamoyl)anthranilic acid (hereinafter referred to as TRANILAST) or a pharmaceutical acceptable salt thereof. More particularly, this invention provides pharmaceutical compositions, such as eye drops and nasal drops for treatment of allergic diseases such as allergic conjunctivitis and allergic rhinitis, containing TRANILAST represented by the formula:

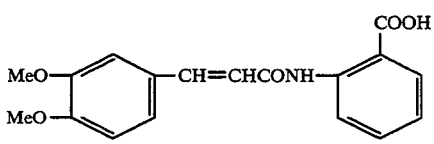

or a pharmaceutically acceptable salt thereof as an active ingredient, a basic compound, polyvinylpyrrolidone and a surface active agent, and having a pH of about 6.5–8.5.

BACKGROUND OF THE INVENTION

It is well known that TRANILAST exhibits antiallergic action (Japanese Patent No. 1096724; U.S. Pat. No. Re. 32,944; U.S. Pat. No. 4,070,484), and thus, TRANILAST is used as a therapeutical agent for the treatment of allergic diseases such as bronchial asthma, atopic dermatitis and the like. However, TRANILAST is so insoluble in water that only pharmaceutical compositions for oral administration have been employed in the treatment of allergic diseases, and any pharmaceutical compositions other than those for oral administration have not been developed as yet.

Recently, a rising number of patients suffering from allergic conjunctivitis and allergic rhinitis have increased the need for pharmaceutical compositions in a form for topical application, such as eye drops and nasal drops containing TRANILAST.

SUMMARY OF THE INVENTION

Accordingly, an object of this invention is to provide pharmaceutical compositions such as eye drops, nasal drops and the like, containing TRANILAST for the treatment of allergic conjunctivitis and rhinitis.

It is a further object of this invention to provide a method for the treatment of allergic conjunctivitis and rhinitis by using a pharmaceutical composition such as eye drops or nasal drops, containing TRANILAST.

Other objects, features and advantages of this invention will be apparent from the following description of the invention.

DETAILED DESCRIPTION OF THE INVENTION

TRANILAST and pharmaceutically acceptable salts thereof are too insoluble in water to prepare an aqueous solution. Until recently any pharmaceutical compositions in an aqueous form have not existed for the treatment of allergic diseases such as allergic conjunctivitis and allergic rhinitis.

Japanese Patent Application Number Sho 63-122698 describes a pharmaceutical composition in an aqueous form containing dissolved TRANILAST in a therapeutic amount which is prepared by employing polyvinylpyrrolidone as a solubilizing aid, in more than 4 times the amount by weight of TRANILAST or a pharmaceutically acceptable salt thereof, in the presence of a basic compound.

However, these aqueous compositions have certain disadvantages. Thus, when a quaternary ammonium salt such as benzalkonium chloride or benzethonium chloride is used as a preservative, a precipitate of insoluble materials occurs in these compositions. Furthermore, if sodium chloride is added to these aqueous compositions to make them isotonic, a precipitate of insoluble materials is evident.

In Japanese patent application Sho 63-122698, it states that this precipitation of insoluble materials from aqueous compositions can be reduced by using a surface active agent. However, the precipitation of insoluble materials from the compositions can not be accomplished completely and reliably solely by utilizing a surface active agent.

Thus, there remains a need for aqueous pharmaceutical compositions for topical application, which are stable in the presence of additives used in making aqueous pharmaceutical compositions adapted for eye drop or nasal drop formulations.

In accordance with the present invention, it has been found that an aqueous solution can be prepared by dissolving TRANILAST in water together with selected quantities by weight of (1) polyvinylpyrrolidone, (2) a basic compound, and (3) a surface active agent, and adjusting the pH of the solution in the range between about 6.5–8.5 by the use of an appropriate reagent such as a buffer. The invention aqueous solution is stable when blended with additives which are used in preparing eye drop and nasal drop solutions, and therefore can be formulated into pharmaceutical compositions such as eye drops and nasal drops for topical application.

A present invention aqueous pharmaceutical composition for topical application can be prepared by admixing TRANILAST, a basic compound and a surface active agent with sterilized water; heating the mixture at a temperature of about 60°–80° C. to form a homogeneous solution; dissolving polyvinylpyrrolidone and a buffer in the solution with heating; optionally adding a preservative and a stabilizing agent to the solution; and diluting the solution with sterilized water to provide a pharmaceutical composition containing TRANILAST at a desired concentration level, e.g., 0.1–2 weight percent, based on the composition volume.

In the preparation of pharmaceutical compositions of this invention, polyvinylpyrrolidone is employed in a quantity between about 4–8 weight units per unit of TRANILAST or pharmaceutically acceptable salt thereof.

Polyvinylpyrrolidone is a polymer having an average molecular weight in the range of about 25,000–40,000. A preferred polyvinylpyrrolidone is one having a weight average molecular weight of about 25,000.

Illustrative of the basic component of the invention aqueous compositions are compounds such as tribasic sodium phosphate, sodium borate, sodium citrate, and the like. The basic component is employed in a quantity between about 0.7–3 weight units per unit of TRANILAST.

As required, the pH of the invention aqueous compositions can be adjusted with a reagent such as acetic acid, phosphoric acid, boric acid, tartaric acid and citric acid or a basic salt thereof. Boric acid is a preferred type of buffering reagent.

Illustrative of the surface active component of the invention aqueous compositions are non-ionic surface active agents having a HLB value of 10–16, such as polyoxyethylene hydrogenated caster oil, polyoxyethylene sorbitan monooleate, polyoxyethylene sorbitan monopalmitate and polyoxyethylene sorbitan monolaurate; and amphoteric surface active agents such as lauryldimethylaminoacetic acid betaine, lauryldimethylamine oxide and laurylcarboxymethylhydroxyethylimidazolinium betaine. Of the different types of surface active agents, non-ionic surface active agents are preferred, and polyoxyethylene sorbitan monooleate (Polysorbate 80, Hart Products; Tween 80, ICI America) is particularly preferred.

In the preparation of invention pharmaceutical compositions, e.g., an eye drop formulation, the quantity of surface active component is minimized to prevent any irritation effect during usage. A suitable concentration of surface active component in an invention aqueous pharmaceutical composition is in the range of about 0.025–0.75 weight percent, based on the composition volume, for non-ionic surface active agents, and in a range of about 0.075–0.1 weight percent for amphoteric surface active agents.

An invention aqueous pharmaceutical composition can contain other constituents such as osmotic pressure adjusting agents, stabilizing agents, preservatives, antioxidants, viscosity control agents, and the like.

The aqueous pharmaceutical compositions of this invention are useful in the treatment of allergic conjunctivitis or allergic rhinitis. The compositions can be formed into stable formulations for eye drop or nasal drop applications, and can be used with safety and comfort without any irritant effects.

The following examples are further illustrative of the present invention. The components and specific ingredients are presented as being typical, and various modifications can be derived in view of the foregoing disclosure within the scope of the invention.

EXAMPLE I

Eye Drop Formulation Containing 0.25% TRANILAST

| TRANILAST | 0.25% |
| --- | --- |
| Boric acid | 1.5% |
| Sodium borate | 0.6% |
| Polyvinylpyrrolidone (K-25) | 1.5% |
| Polysorbate 80 | 0.05% |
| Benzalkonium chloride | 0.005% |
| Sodium edetate | 0.01% |
| Water | 100 ml volume |

A mixture of 0.25 g of TRANILAST, 0.18 g of sodium borate and 0.05 g of polysorbate 80 was added to about 50 ml of sterilized water, and was heated at 60°–80° C. to form a clear solution.

This was followed by the successive addition of 1.5 g of polyvinylpyrrolidone (K-25), 1.5 g of boric acid, 0.42 g of sodium borate, 0.005 g of benzalkonium chloride and 0.01 g of sodium edetate, and then sterilized water was added to a total volume of 100 ml. The aqueous solution contained 0.25% of TRANILAST, and had a pH of 7.4 and an osmotic pressure ratio of about 1.0.

EXAMPLE II

Eye Drop Formulation Containing 0.5% TRANILAST

| TRANILAST | 0.5% |
| --- | --- |
| Boric acid | 1.3% |
| Sodium borate | 0.75% |
| Polyvinylpyrrolidone (K-25) | 3% |
| Polysorbate 80 | 0.05% |
| Benzalkonium chloride | 0.005% |
| Sodium edetate | 0.01% |
| Water | 100 ml volume |

A mixture of 0.5 g of TRANILAST, 0.35 g of sodium borate and 0.05 g of polysorbate 80 was added to about 50 ml of sterilized water and was heated at 60°–80° C. to form a clear solution.

This was followed by the successive addition of 3.0 g of polyvinylpyrrolidone (K-25), 1.3 g of boric acid, 0.4 g of sodium borate, 0.005 g benzalkonium chloride and 0.01 g of sodium edetate, and then sterilized water was added to a total volume of 100 ml. The aqueous solution contained 0.5% of TRANILAST, and had a pH of 7.4 and an osmotic pressure ratio of about 1.0.

EXAMPLE III

Eye Drop Formulation Containing 1% TRANILAST

| TRANILAST | 1% |
| --- | --- |
| Boric acid | 0.9% |
| Sodium borate | 0.9% |
| Polyvinylpyrrolidone (K-25) | 6% |
| Polysorbate 80 | 0.05% |
| Benzalkonium chloride | 0.005% |
| Sodium edetate | 0.01% |
| Water | 100 ml volume |

Following the formulation procedures previously described, an eye drop solution was prepared which contained 1% of TRANILAST, and had a pH of 7.4 and about a 1.0 osmotic pressure ratio relative to a 0.9 w/v % sodium chloride aqueous solution having about 290 millimoles.

The osmotic pressure was measured in accordance with the freezing-point depression method described on pages 1595–1597 of the "Supplement to the Pharmacopoeia of Japan", Eleventh Edition, 1988.

An osmometer was calibrated by a two-point calibration method using two different standard solutions of 100 milliosmoles and 500 milliosmoles. The osmotic pressures of a test sample and a 0.9 w/v % sodium chloride aqueous solution were measured:

$$\text{osmotic pressure ratio} = \frac{O_T}{O_S}$$

where $O_T$ is the osmotic pressure of the test sample, and $O_S$ is the osmotic pressure of the sodium chloride aqueous solution.

What is claimed is:

1. A pharmaceutical composition for the topical treatment of eye or nose allergic conjunctivitis or allergic rhinitis which consists essentially of an aqueous solution containing (a) 0.1–2 weight percent, based on the composition volume, of N-(3,4-dimethoxycinnamoyl)anthranilic acid or a pharmaceutically acceptable salt thereof; (b) about 4–8 weight units of polyvinylpyrrolidone per weight unit of the N-(3,4-dimethoxycinnamoyl)anthranilic acid component; (c) about 0.7–3 weight units of a basic compound per weight unit of the N-(3,4-dimethoxycinnamoyl)anthranilic acid component; (d) about 0.025–0.1 weight percent, based on the composition volume, of a surface active agent; and (e) a preservative quantity of benzalkonium chloride or benzethonium chloride; wherein the aqueous solution has a buffered pH in the range of about 6.5–8.5, and is precipitate-free.

2. A pharmaceutical composition in accordance with claim 1 wherein the surface active agent is between about monooleate.

3. A pharmaceutical composition in accordance with claim 1 which contains sodium edetate as an additional ingredient.

* * * * *

UNITED STATES PATENT AND TRADEMARK OFFICE
CERTIFICATE OF CORRECTION

PATENT NO. : 5,356,620
DATED : October 18, 1994
INVENTOR(S) : Yamamoto et al

It is certified that error appears in the above-indentified patent and that said Letters Patent is hereby corrected as shown below:

Claim 2, 3rd line, (Col. 6, line 6), after "about" insert

-- 0.025-0.75 weight percent of polyoxyethylene sorbitan --

Signed and Sealed this

Twenty-fourth Day of January, 1995

Attest:

BRUCE LEHMAN

Attesting Officer     Commissioner of Patents and Trademarks